(12) United States Patent
Makino (10) Patent No.: US 12,150,622 B2
(45) Date of Patent: Nov. 26, 2024

(54) PROCESSOR FOR ENDOSCOPE AND ENDOSCOPIC SYSTEM

(71) Applicant: HOYA CORPORATION, Tokyo (JP)

(72) Inventor: Takao Makino, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 365 days.

(21) Appl. No.: 17/789,931

(22) PCT Filed: Jun. 30, 2021

(86) PCT No.: PCT/JP2021/024861
§ 371 (c)(1),
(2) Date: Jun. 29, 2022

(87) PCT Pub. No.: WO2022/059293
PCT Pub. Date: Mar. 24, 2022

(65) Prior Publication Data
US 2023/0041803 A1 Feb. 9, 2023

(30) Foreign Application Priority Data
Sep. 15, 2020 (JP) ................. 2020-154912

(51) Int. Cl.
*H04N 5/20* (2006.01)
*A61B 1/00* (2006.01)
(Continued)

(52) U.S. Cl.
CPC .......... *A61B 1/04* (2013.01); *A61B 1/000095* (2022.02); *H04N 5/20* (2013.01);
(Continued)

(58) Field of Classification Search
None
See application file for complete search history.

(56) References Cited

U.S. PATENT DOCUMENTS

| 2010/0182414 A1 | 7/2010 | Suzuki |
| 2018/0214005 A1* | 8/2018 | Ebata ................. A61B 5/02007 |

(Continued)

FOREIGN PATENT DOCUMENTS

| JP | 2005-73718 A | 3/2005 |
| JP | 2011-120731 A | 6/2011 |

(Continued)

OTHER PUBLICATIONS

International Search Report issued in International Bureau of WIPO Patent Application No. PCT/JP2021/024861, dated Aug. 3, 2021, along with an English translation thereof.

*Primary Examiner* — James M Hannett
(74) *Attorney, Agent, or Firm* — GREENBLUM & BERNSTEIN, P.L.C.

(57) ABSTRACT

An image processing unit of a processor for an endoscope includes: an emphasis processing calculation unit performing nonlinear gradation conversion for a pixel value of a pixel of interest, using each pixel of a captured image as the pixel of interest; and a preprocessing unit setting a reference upper limit characteristic line and a reference lower limit characteristic line in order to adjust an output pixel value after the nonlinear gradation conversion and calculating a degree of variation in pixel values in a partial setting region around the pixel of interest. The emphasis processing calculation unit calculates an output ratio of the output pixel value to a maximum pixel value that can be taken by the captured image, an adjustment upper limit value and an adjustment lower limit value, and an emphasis-processed pixel value, using the adjustment upper limit value, the adjustment lower limit value, and the output ratio.

12 Claims, 5 Drawing Sheets

(51) Int. Cl.
  *A61B 1/04* (2006.01)
  *H04N 23/50* (2023.01)
  *H04N 23/82* (2023.01)
  *H04N 7/18* (2006.01)

(52) U.S. Cl.
  CPC .......... *H04N 23/555* (2023.01); *H04N 23/82* (2023.01); *H04N 7/18* (2013.01)

(56) References Cited

U.S. PATENT DOCUMENTS

| | | | |
|---|---|---|---|
| 2018/0228347 A1* | 8/2018 | Yamamoto | A61B 1/00057 |
| 2018/0235527 A1* | 8/2018 | Yamamoto | A61B 1/00188 |
| 2020/0405152 A1 | 12/2020 | Hirano et al. | |
| 2021/0201486 A1 | 7/2021 | Takenouchi | |

FOREIGN PATENT DOCUMENTS

| | | |
|---|---|---|
| JP | 5006759 B2 | 8/2012 |
| JP | 5966603 B2 | 8/2016 |
| WO | 2008/149952 A1 | 12/2008 |
| WO | 2019/230095 A1 | 12/2019 |
| WO | 2020/067105 A1 | 4/2020 |

* cited by examiner

PROCESSOR FOR ENDOSCOPE AND ENDOSCOPIC SYSTEM

TECHNICAL FIELD

The present invention relates to a processor for an endoscope including an image processing unit that applies gradation conversion to a captured image of a living tissue in a body cavity and an endoscope system.

BACKGROUND ART

An endoscope is used to observe or treat a living tissue inside a human body. An image of a living tissue captured using the endoscope and displayed on a display is often an image to which image processing has been applied so that a living tissue of interest or a part of the living tissue can be more easily visually recognized than other parts. The image processing includes processing of emphasizing contrast, processing of brightening the entire image, processing of changing a color tone, and emphasis processing of performing gradation conversion to widen the number of gradations in a range of a predetermined gradation level.

For example, in the emphasis processing, a tone curve for changing and outputting the gradation level of an input image is often set. Such a tone curve is stored and retained in advance, and at the time of the emphasis processing, the stored and retained tone curve is called and the emphasis processing is applied to the image obtained by the endoscope. Therefore, how to perform the emphasis processing is determined by the tone curve.

For example, a technique of an electronic endoscope device capable of obtaining an image in which a blood vessel is sufficiently emphasized while using white light is known (see Japanese Patent No. 5006759).

The technique includes an RGB conversion means that converts an image signal into an RGB signal, an R signal amplification means that increases or decreases an R signal of the RGB signal with a constant gain, and a GB signal amplification means that nonlinearly increases or decreases a G signal and a B signal of the RGB signal. At this time, the gains in the R signal amplification means and the GB signal amplification means are stored as unique values for each part to be observed, and the gain is selected on the basis of the part to be observed.

Further, a technique of image processing capable of accurately converting brightness of each pixel even in an image having continuous brightness is also known (see Japanese Patent No. 5006759).

In the technique, an upper limit conversion function and a lower limit conversion function that determine an output upper limit and an output lower limit of brightness conversion are determined according to brightness of each pixel in a local region in a captured image, an upper limit value and a lower limit value of the brightness are calculated using the two conversion functions, a ratio for setting a value between the upper limit value and the lower limit value is further calculated from the upper limit value and the lower limit value according to the brightness of each pixel, and a value after brightness conversion is calculated using the calculated upper limit value, lower limit value, and ratio (see Japanese Patent No. 5966603).

SUMMARY OF INVENTION

Technical Problem

In the above-described technique of the electronic endoscope device, the contrast of the image decreases in a portion where the change in the tone curve is gentle. Therefore, for example, in a portion such as a dark portion, an image to be originally identified is collapsed and there is a disadvantage that the identification is difficult.

Meanwhile, in the above-described image processing technology, in the brightness conversion, a noise component in the image is emphasized in a portion where the brightness value rapidly changes, and thus, black dots may be scattered in a flat portion (for example, a white region having high luminosity) in the image after the conversion.

Therefore, an object of the present invention is to provide a processor for an endoscope and an endoscope system capable of suppressing emphasis of noise in a flat portion in an image without collapsing an image of a portion such as a dark portion that is conventionally likely to be collapsed when performing emphasis processing by performing gradation conversion for a captured image.

Solution to Problem

One aspect of the present invention is a processor for an endoscope including an image processing unit that applies gradation conversion to a captured image of a living tissue in a body cavity. The image processing unit of the processor for an endoscope includes an emphasis processing calculation unit configured to perform emphasis processing of an input captured image by performing nonlinear gradation conversion for a pixel value of a pixel of interest of the captured image, and a preprocessing unit configured to set, for the input pixel value, a reference upper limit characteristic line representing a reference adjustment upper limit value of an output pixel value for adjusting the output pixel value output by the nonlinear gradation conversion and a reference lower limit characteristic line representing a reference adjustment lower limit value of the output pixel value for adjusting the output pixel value, set a partial setting region including the pixel of interest in the captured image, and calculate a degree of variation in pixel values in the partial setting region The emphasis processing calculation unit
calculates an output ratio of the output pixel value to a maximum pixel value that the captured image is able to take by inputting the pixel value and performing the nonlinear gradation conversion,
calculates an adjustment upper limit value and an adjustment lower limit value by adjusting the reference adjustment upper limit value and the reference adjustment lower limit value obtained using the reference upper limit characteristic line and the reference lower limit characteristic line according to the degree of variation in pixel values by inputting the pixel value, and
calculates a value of a division point for dividing the adjustment upper limit value and the adjustment lower limit value by the output ratio, and outputs the calculated value of the division point as an emphasis-processed pixel value.

Further, another aspect of the present invention is also a processor for an endoscope including an image processing unit that applies gradation conversion to a captured image of a living tissue in a body cavity. The image processing unit of the processor for an endoscope includes
an emphasis processing calculation unit configured to perform emphasis processing of an input captured image by performing nonlinear gradation conversion for a pixel value of a pixel of interest in a partial setting region of the captured image, and a preprocessing unit configured to calculate a degree of variation in the pixel values in the partial setting region of the captured image, and The emphasis processing calculation unit sets, for the input pixel value, an upper limit characteristic line representing an adjustment upper limit value of an output pixel value for adjusting the output pixel value output by the nonlinear gradation conversion and a lower limit characteristic line representing an adjustment lower limit value of the output pixel value for adjusting the output pixel value according to the degree of variation in the pixel values in the partial setting region, calculates an output ratio of the output pixel value to a maximum pixel value that the captured image is able to take by inputting the pixel value and performing the nonlinear gradation conversion, calculates the adjustment upper limit value and the adjustment lower limit value using the upper limit characteristic line and the lower limit characteristic line by inputting the pixel value, and calculates a value of a division point for dividing the adjustment upper limit value and the adjustment lower limit value by the output ratio, and outputs the calculated value of the division point as an emphasis-processed pixel value.

It is favorable that the upper limit characteristic line and the lower limit characteristic line are lines obtained by expanding or contracting a reference upper limit characteristic line and a reference lower limit characteristic line serving as references toward an output side according to the degree of variation.

It is favorable that each of a plurality of predetermined block regions in the captured image is set as the partial setting region.

It is favorable that the value of the division point is a weighted average value of the adjustment upper limit value and the adjustment lower limit value using the output ratio and a residual ratio obtained by subtracting the output ratio from 1 as weighting coefficients.

It is favorable that a difference between the adjustment upper limit value and the adjustment lower limit value increases as the variation increases.

It is favorable that the adjustment lower limit value decreases as the variation increases.

It is favorable that the adjustment upper limit value increases as the variation increases.

It is favorable that a change rate of the adjustment upper limit value with respect to a change in the input pixel value increases as the variation increases, and a change rate of the adjustment lower limit value with respect to a change in the input pixel value decreases as the variation increases.

It is favorable that the nonlinear gradation conversion is set on a basis of a distribution of pixel values in the partial setting region.

It is favorable that the captured image includes pixel values of a plurality of color components, and the processing and calculation in the preprocessing unit and the emphasis processing calculation unit are performed for each of the color components.

Another aspect of the present invention is an endoscope system including the processor for an endoscope, and an endoscope connected to the processor for an endoscope and including an image sensor that captures the living tissue.

Advantageous Effects of Invention

According to the processor for an endoscope and the endoscope system of the present invention, when emphasis processing is performed by performing gradation conversion for a captured image, emphasis of noise can be suppressed in a flat portion in an image without collapsing an image of a portion such as a dark portion that is conventionally likely to be collapsed.

DESCRIPTION OF EMBODIMENTS

Figure 1:
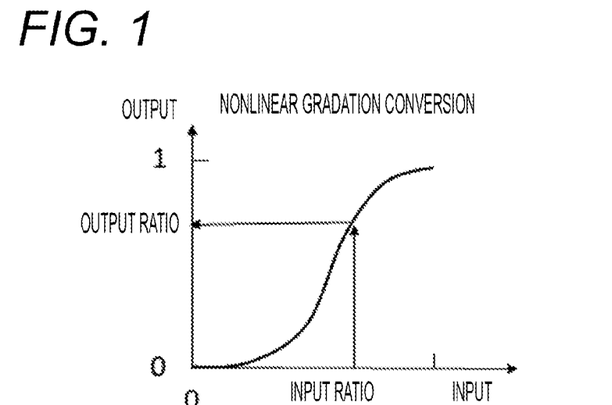
FIG. 1 is a diagram for describing nonlinear gradation conversion performed by a processor for an endoscope of an endoscope system according to an embodiment.
Figure 2:
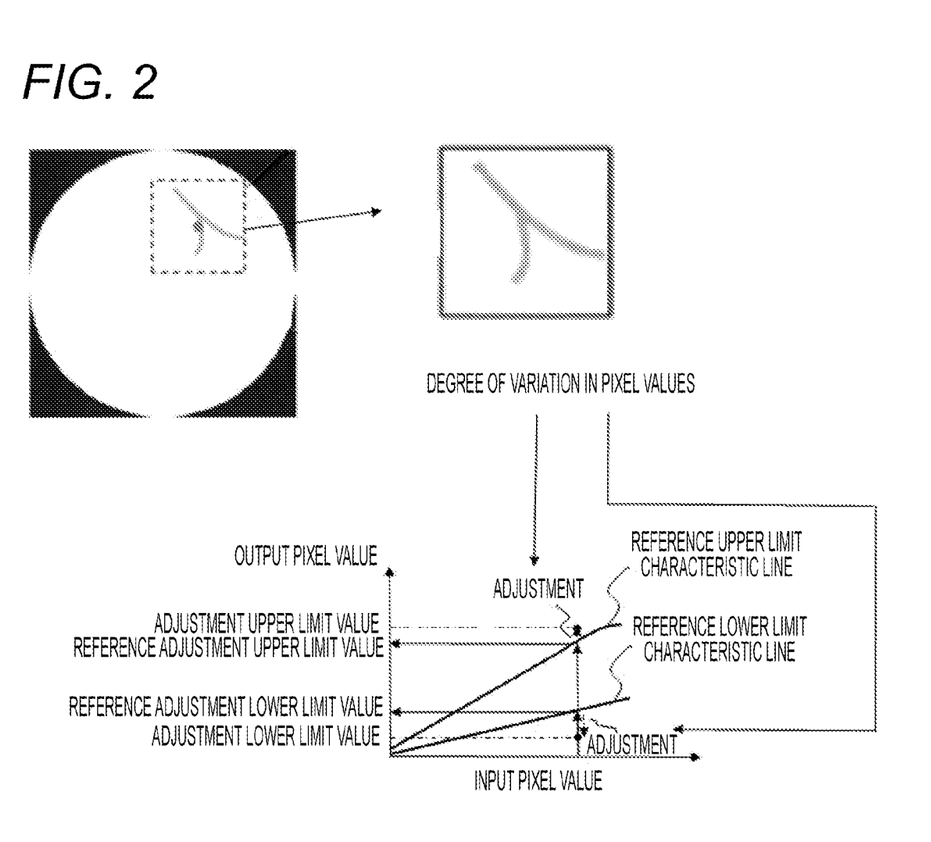
FIG. 2 is a diagram for describing a partial setting region, a reference upper limit characteristic line, and a reference lower limit characteristic line set by the processor for an endoscope of the endoscope system according to the embodiment.
Figure 3:
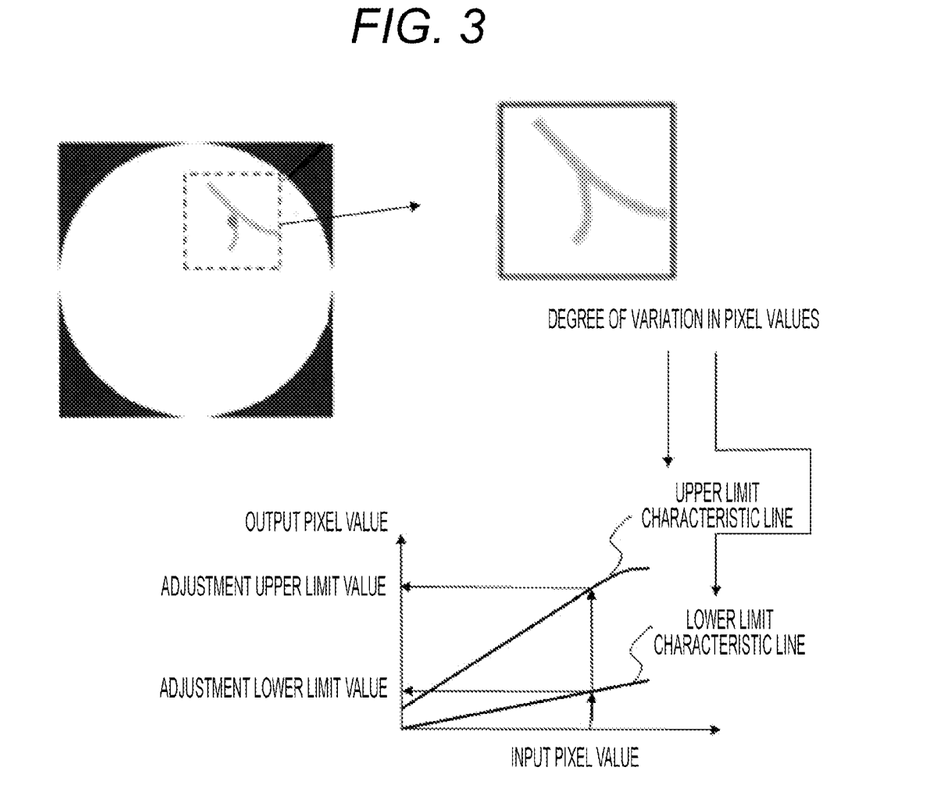
FIG. 3 is a diagram for describing a method different from a method of calculating the adjustment upper limit value and the adjustment lower limit value illustrated in FIG. 2.
Figure 4:
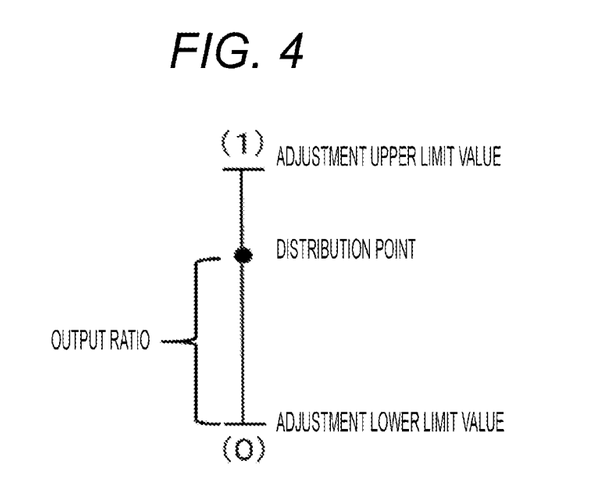
FIG. 4 is a diagram for describing calculation processing of emphasis processing performed by a processor for an endoscope of the endoscope system according to the embodiment.

Hereinafter, embodiments of the present invention will be described with reference to drawings. FIG. 1 is a diagram for describing nonlinear gradation conversion performed by a processor for an endoscope of an endoscope system according to an embodiment. FIG. 2 is a diagram for describing a partial setting region, a reference upper limit characteristic line, and a reference lower limit characteristic line set by the processor for an endoscope of the endoscope system according to the embodiment. FIG. 3 is a diagram for describing a method different from a method of calculating the adjustment upper limit value and the adjustment lower limit value illustrated in FIG. 2. FIG. 4 is a diagram for describing calculation processing of emphasis processing performed by a processor for an endoscope of the endoscope system according to the embodiment.

The processor for an endoscope according to the present embodiment performs emphasis processing for a captured image captured by an endoscope using nonlinear gradation conversion. Hereinafter, the emphasis processing using the nonlinear gradation conversion will be described. The emphasis processing using the nonlinear gradation conversion is performed by an image processing unit of the processor for an endoscope as will be described below, and more specifically, calculation of variation in pixel values in a partial region to be described below is performed by a preprocessing unit (see FIG. 5) of the processor for an endoscope, and calculation of an adjustment upper limit value and an adjustment lower limit value and the emphasis processing using an output ratio to be described below obtained by the nonlinear gradation conversion, the adjustment upper limit value, and the adjustment lower limit value are performed by an emphasis processing calculation unit (see FIG. 5) of the processor for an endoscope.

(Emphasis Processing Using Nonlinear Gradation Conversion)

As illustrated in FIG. 1, the emphasis processing calculation unit performs the nonlinear gradation conversion for a pixel value in a captured image of a living tissue in a body cavity captured by the endoscope. In the example illustrated in FIG. 1, a conversion curve of the nonlinear gradation conversion is indicated by an output ratio with respect to an input ratio. The input ratio and the output ratio are ratios of an input pixel value or an output pixel value after the nonlinear conversion to a maximum pixel value that can be taken by the pixel value of the captured image. The pixel value of the captured image is represented by, for example, a gradation value of 0 to 255 in a case where AD conversion is performed in 8 bits. In the example illustrated in FIG. 1, the output ratio with respect to the input ratio is represented as the conversion curve of the nonlinear gradation conversion, but the conversion curve may be represented by a curve of the output pixel value with respect to the input pixel value.

Meanwhile, in one embodiment, as illustrated in FIG. 2, each pixel in the input image is used as a pixel of interest, and a partial setting region is set for the pixel of interest. The partial setting region is, for example, a region within a predetermined frame having the pixel of interest in the captured image as a center pixel, for example, a rectangular frame region. Therefore, the partial setting region is set for each pixel of interest. The pixel of interest moves so as to scan the captured image pixel by pixel.

In another embodiment, the partial setting region is not set according to the pixel of interest, and may be preset as a preset region. For example, the partial setting region is set by the preprocessing unit when a user who views the captured image displayed on a display connected to the processor for an endoscope instructs an input of a region where the emphasis processing is to be performed using an input operation device such as a mouse. Other than by being set by the input of the user, the partial setting region may be configured such that the preprocessing unit automatically sets a portion where the image is likely to be collapsed by the nonlinear gradation conversion or a portion where noise included in the pixel value is likely to stand out as the partial setting region by analyzing the pixel value of the captured image.

Moreover, the degree of variation in pixel values in the set partial setting region is calculated by the preprocessing unit. Examples of the degree of variation in pixel values include variance, standard deviation, absolute deviation, and difference between the maximum pixel value and a minimum pixel value of the pixel values. The degree of variation in pixel values is used for calculation of the adjustment upper limit value and the adjustment lower limit value to be described below.

A reference upper limit characteristic line illustrated in FIG. 2 is a line representing a reference adjustment upper limit value of the output pixel value for adjusting the output pixel value output by the nonlinear gradation conversion with respect to the input pixel value. A reference lower limit characteristic line is a line representing a reference adjustment lower limit value of the output pixel value for adjusting the output pixel value. As illustrated in FIG. 2, the reference upper limit characteristic line and the reference lower limit characteristic line are represented by the output pixel values with respect to the input pixel values. Forms of the reference upper limit characteristic line and the reference lower limit characteristic line are favorably forms in which the output pixel value is maintained constant or increases as the input pixel value increases, and are favorably a so-called monotonic increase in which the output pixel value increases as the input pixel value increases. In the case that the pixel value of the captured image is represented by the gradation value of 0 to 255, the reference upper limit characteristic line is set such that the output pixel value becomes 255 in the case where the input pixel value is 255, namely, the output pixel value also becomes a maximum gradation value when the input pixel value is a maximum gradation value. In the case that the pixel value of the captured image is represented by the gradation value of 0 to 255, the reference lower limit characteristic line is set such that the output pixel value becomes 0 in the case where the input pixel value is 0, namely, the output pixel value also becomes a minimum gradation value when the input pixel value is a minimum gradation value. Moreover, the reference lower limit characteristic line is set to be positioned on a side where the output pixel value is smaller than that of the reference upper limit characteristic line. In this case, when the input pixel value is near the minimum gradation value, a gradient of the reference lower limit characteristic line is favorably gentler than a gradient of the reference upper limit characteristic line. In the reference upper limit characteristic line, the output pixel value does not need to pass through the minimum gradation value in the case where the input pixel value is the minimum gradation value, and in the reference lower limit characteristic line, the output pixel value does not need to pass through the maximum gradation value in the case where the input pixel value is the maximum gradation value.

Such reference upper limit characteristic line and the reference lower limit characteristic line may be straight lines, curved lines, or combinations of straight lines and curved lines. The reference upper limit characteristic line and the reference lower limit characteristic line may be represented by a preset function.

Such reference upper limit characteristic line and the reference lower limit characteristic line are preset in the preprocessing unit.

As illustrated in FIG. 2, the reference upper limit characteristic line and the reference lower limit characteristic line are used to calculate the reference adjustment upper limit value and the reference adjustment lower limit value. As illustrated in FIG. 2, when the pixel value of the pixel of interest is input as the input pixel value, the reference adjustment upper limit value and the reference adjustment lower limit value corresponding to the input pixel value (input pixel value) are calculated from the reference upper limit characteristic line and the reference lower limit characteristic line.

Moreover, the adjustment upper limit value and the adjustment lower limit value are calculated by adjusting the calculated reference adjustment upper limit value and reference adjustment lower limit value according to the degree of variation in pixel values in the partial setting region calculated by the preprocessing unit. For example, the adjustment upper limit value adjusted in such a manner that the value becomes larger with respect to the reference adjustment upper limit value as the variation in pixel values becomes larger is calculated, and the adjustment lower limit value adjusted in such a manner that the value becomes smaller with respect to the reference adjustment lower limit value as the variation in pixel values becomes larger is calculated.

In the above-described embodiment, the reference upper limit characteristic line and the reference lower limit characteristic line are determined in advance, the reference adjustment upper limit value corresponding to the input pixel value is calculated from the reference upper limit characteristic line and the reference adjustment lower limit value corresponding to the input pixel value is calculated from the reference lower limit characteristic line using the input pixel value of the pixel of interest, and the adjustment upper limit value and the adjustment lower limit value are calculated by adjusting the reference adjustment upper limit value and the reference adjustment lower limit value according to the degree of variation in the pixel value in the partial setting region. However, as described above, in a case where the partial setting region is not set according to the pixel of interest and a prefixed region is set in advance, the adjustment upper limit value and the adjustment lower limit value corresponding to the input pixel value may be calculated by fixing an upper limit characteristic line and a lower limit characteristic line set according to the variation in pixel values in the partial setting region as the adjustment upper limit value and the adjustment lower limit value as illustrated in FIG. 3. The upper limit characteristic line is adjusted to increase the adjustment upper limit value, for example, in a case where the degree of variation in pixel values in the partial setting region is large, and the lower limit characteristic line is adjusted to decrease the adjustment lower limit value, for example, in a case where the degree of variation in pixel values in the partial setting region is large. In a case where the upper limit characteristic line and the lower limit characteristic line are represented by set functions, it is favorable to use numerical values representing variations in pixel values as parameters for changing the functions. In this case, the parameters are favorably incorporated into the functions such that, for example, the adjustment upper limit value is large and the adjustment lower limit value is small in the case where the degree of variation is large depending on the numerical value representing the degree of variation.

Forms of the upper limit characteristic line and the lower limit characteristic line are favorably forms in which the output pixel value is maintained constant or increases as the input pixel value increases. The upper limit characteristic line is set such that the output pixel value also becomes the maximum gradation value in the case where the input pixel value is the maximum gradation value. The lower limit characteristic line is set such that the output pixel value also becomes the minimum gradation value in the case where the input pixel value is the minimum gradation value. Moreover, the lower limit characteristic line is set to be positioned on a side where the output pixel value is smaller than that of the upper limit characteristic line. In this case, when the input pixel value is near the minimum gradation value, the gradient of the lower limit characteristic line is favorably gentler than the gradient of the upper limit characteristic line.

In the emphasis processing calculation unit, the output ratio calculated by inputting the pixel value and performing the nonlinear gradation conversion and the adjustment upper limit value and the adjustment lower limit value calculated by the method illustrated in FIG. 2 or 3 are used to calculate a value of a division point for dividing the adjustment upper limit value and the adjustment lower limit value by the output ratio, and the calculated value of the division point is output as an emphasis-processed pixel value.

As illustrated in FIG. 4, when the adjustment upper limit value is 1 and the adjustment lower limit value is 0, the output ratio, which is a value between 0 to 1, is set as a division point for dividing 0 to 1, the value of the division point between the adjustment upper limit value and the adjustment lower limit value is calculated, and the value at this division point is output as the emphasis-processed pixel value.

That is, a possible range that can be taken by the pixel value is determined by the adjustment upper limit value and the adjustment lower limit value determined according to the variation in pixel values in the partial setting region, and the value corresponding to the output ratio in the possible range of values is set as the emphasis-processed pixel value. For example, in a case where the adjustment upper limit value is 150, the adjustment lower limit value is 50, and the output ratio is 0.4, the value corresponding to the output ratio 0.4 is 90 (=(150−50)*0.4+50). This value is set as the emphasis-processed pixel value.

Therefore, in the case where the possible range of the pixel value is, for example, 0 to 255, and in the case where the adjustment upper limit value is set to 255 and the adjustment lower limit value is set to 0, the emphasis-processed pixel value is the same as the pixel value obtained by the nonlinear gradation conversion, but the adjustment upper limit value and the adjustment lower limit value change according to the degree of variation in pixel values in the partial setting region and thus become values different from the pixel value obtained by the nonlinear gradation conversion. That is, the emphasis-processed pixel value changes according to a change in the adjustment upper limit value and the adjustment upper limit value according to the degree of variation in pixel values in the partial setting region.

Therefore, when the emphasis processing is performed by performing the gradation conversion for the captured image, a portion such as a dark portion where the image is likely to be collapsed is set as the partial setting region, or a portion where noise is emphasized by the nonlinear gradation conversion is set as the partial setting region, so that the adjustment upper limit value and the adjustment lower limit value that change according to the degree of variation in pixel values in the partial setting region are determined. The pixel value after the emphasis processing is calculated using the adjustment upper limit value and the adjustment lower limit value, and the output ratio calculated by the nonlinear gradation conversion. Therefore, it is possible to perform the emphasis processing in which noise is less likely to be emphasized in the flat portion in the image without collapsing the image of a portion such as a dark portion where the image is likely to be collapsed.

(Endoscope System)

Figure 5:
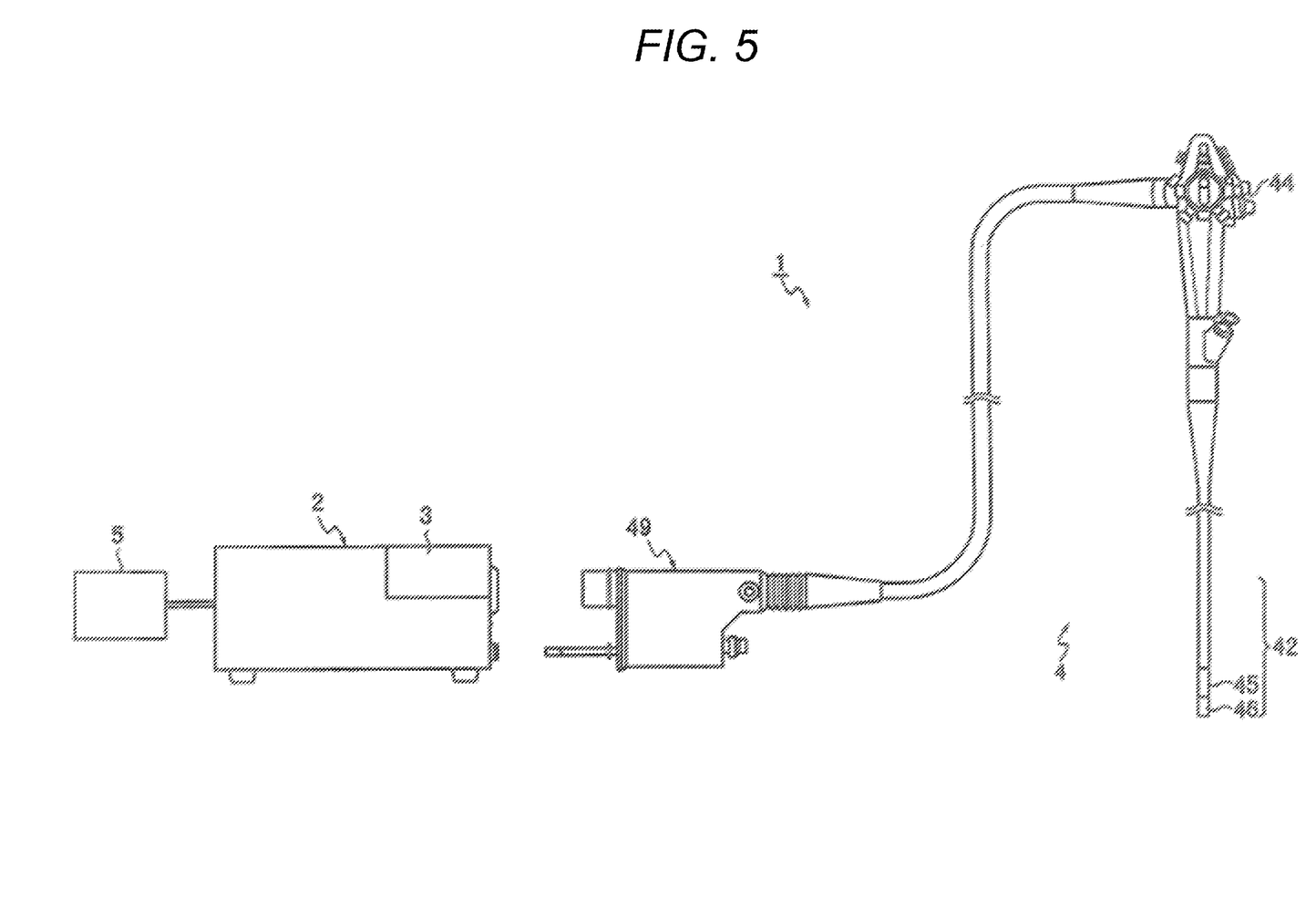
FIG. 5 is an external perspective view of the endoscope system according to the embodiment.
Figure 6:
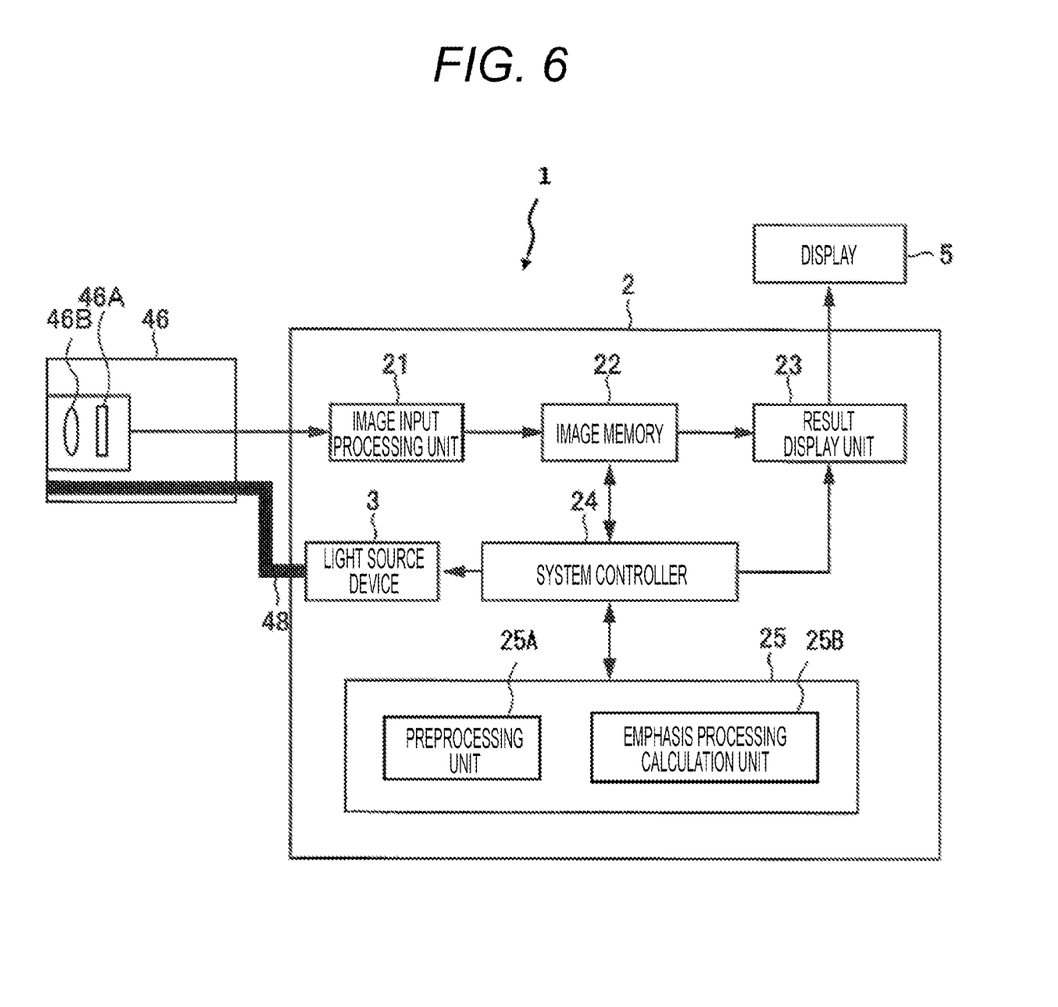
FIG. 6 is a block configuration diagram illustrating a main configuration of the endoscope system according to the embodiment.

FIG. 5 is an external perspective view of an endoscope system 1 of the present embodiment, and FIG. 6 is a block configuration diagram illustrating a main configuration of the endoscope system 1.

The endoscope system 1 mainly includes a processor for an endoscope (hereinafter simply referred to as a processor) 2, a light source device 3, an endoscope 4, and a display 5. The light source device 3, the endoscope 4, and the display 5 are each connected to the processor 2. Note that the light source device 3 and the processor 2 are separately configured but the light source device 3 may be provided in the processor 2.

The light source device 3 emits white light or light of a plurality of wavelength bands. The light source device 3 includes, for example, a white light source such as a light emitting diode (LED) light source, a halogen lamp, or a high intensity lamp such as a metal halide lamp. Further, the light source device 3 may be configured to sequentially output light filtered by each of a plurality of optical filters by rotating a rotating plate in which the plurality of optical filters is arranged and switching the optical filters passing through an optical path of emitted light from the white light source. In this case, although not illustrated, the light source device 3 includes, for example, a lamp power source driver, a light source, a condenser lens, a filter turret, a motor, and a motor driver. In addition, the light source device 3 may include a plurality of semiconductor light emitting elements such as light emitting diodes or laser diodes that emit light in various wavelength bands.

As illustrated in FIG. 5, an insertion portion 42 having flexibility and configured to be inserted into the human body is provided at a distal end of the endoscope 4. In the vicinity of a distal end of the insertion portion 42, a bending portion 45 that is bent in accordance with a remote operation from a hand operation unit 44 connected to a proximal end of the insertion portion 42 is provided. A bending mechanism of the bending portion 45 is a known mechanism incorporated in a general endoscope. The bending structure bends the bending portion 45 by pulling an operation wire in conjunction with a rotation operation of a bending operation knob provided in the hand operation unit 44. A distal end portion 46 including an image sensor 46A (see FIG. 6) is connected to a distal end of the bending portion 45. When the direction of the distal end portion 46 is changed according to the bending operation of the bending portion 45 by the rotation operation of the bending operation knob, an imaging region by the endoscope 4 is moved.

The endoscope 4 includes a light guide 48 (see FIG. 6) arranged over substantially the entire length from a connector unit 49 to the distal end portion 46. The light guide 48 is an optical fiber bundle, and guides irradiation light supplied from the light source device 3 to the distal end portion 46 of the electronic endoscope 4.

Although not illustrated, the distal end portion 46 of the electronic endoscope 4 includes a light distribution lens provided in front of a distal end of the light guide 48, an objective lens 46B (see FIG. 6) that forms an image of the living tissue, an image sensor 46A (see FIG. 6) that receives the formed image, an amplifier (not illustrated) that amplifies an image signal output from the image sensor 46A, and the like.

The light distribution lens is arranged to face a distal end surface of the light guide 48, and diverges the irradiation light emitted from the distal end surface of the light guide 48 to illuminate the living tissue as an object.

The objective lens 46B condenses scattered light or reflected light from the living tissue to form an image of the object on a light receiving surface of the image sensor 46A.

As the image sensor 46A, a CCD image sensor or a CMOS image sensor is suitably used.

An imaging signal output from the image sensor 46A is amplified by the amplifier (not illustrated) and then sequentially transmitted to the connector unit 49.

The connector unit 49 is connected to the processor 2. The connector unit 49 may include a circuit having the following functions. For example, the connector unit 49 may include a circuit that supplies a drive signal to the image sensor 46A to drive the image sensor 46A, AD-converts an analog signal output from the image sensor 46A into a digital signal, and transmits the digital signal to the processor 2 as a signal of a captured image. Further, the circuit may have a function to access a memory (not illustrated) provided in the connector unit 49, read specific information of the endoscope 4, and output the specific information to the processor 2.

The processor 2 is a device that further processes the signal of the captured image obtained by imaging the living tissue by the image sensor 46A of the endoscope, and supplies the signal to the display 5.

The processor 2 is provided with a connector unit (not illustrated) for connection with the endoscope 4. When the connector unit and the connector unit 49 are mechanically connected, the endoscope 4 and the processor 2 are electrically connected, and the light source device 3 and the endoscope 4 are optically connected.

The processor 2 includes an image input processing unit 21, an image memory 22, a result display unit 23, a system controller 24, and an image processing unit 25. FIG. 6 illustrates a configuration in which the replaceable light source device 3 is provided in a housing in which the processor 2 is provided.

The system controller 24 manages and controls operations of the image input processing unit 21, the image memory 22, the result display unit 23, and the image processing unit 25, and controls operations of the light source device 3 and the endoscope 4. The processor 2 includes a memory (not illustrated) that stores information and data in addition to the image memory 22.

The image input processing unit 21 is a unit that applies predetermined signal processing such as color correction and matrix calculation to the signal of the image of the living tissue. A signal-processed video signal is transmitted as the captured image for each pixel to the image memory 22 that is a frame memory, and is temporarily stored.

Moreover, the image stored in the image memory 22 is called for the emphasis processing, and is sent to the image processing unit 25 via the system controller 24 according to an instruction from the system controller 24. Processing in the image processing unit 25 will be described below.

The image processed by the image processing unit 25 is sent to the image memory 22 again and stored therein.

The result display unit 23 calls the image stored in the image memory 22, performs signal processing (γ correction and the like) for the signal of the image to generate an image signal for monitor display, and converts the generated image signal into a predetermined video format signal. The converted video format signal is output to the display 5. As a result, the captured image of the living tissue is displayed on a display screen of the display 5.

In such a processor 2, the image processing unit 25 is configured to perform the emphasis processing for the captured image of the living tissue. Hereinafter, description will be given on the basis of the method of setting the adjustment upper limit value and the adjustment lower limit value as illustrated in FIG. 2.

As illustrated in FIG. 6, the image processing unit 25 includes a preprocessing unit 25A and an emphasis processing calculation unit 25B. The preprocessing unit 25A sets the partial setting region as illustrated in FIG. 2, which is used to perform the above-described emphasis processing using the nonlinear gradation conversion, for each pixel of interest, and calculates the variation in pixel values in the partial setting region. Moreover, the preprocessing unit 25A sets the reference upper limit characteristic line and the reference lower limit characteristic line.

As illustrated in FIG. 1, the emphasis processing calculation unit 25B calculates the output ratio of the output pixel value to the maximum pixel value that can be taken by the captured image by inputting the pixel value and performing the nonlinear gradation conversion. In the example illustrated in FIG. 1, the output ratio is calculated using the input ratio that is the ratio of the input pixel value to the maximum pixel value.

Moreover, as illustrated in FIG. 2, the emphasis processing calculation unit 25B calculates the reference adjustment upper limit value and the reference adjustment lower limit value using the reference upper limit characteristic line and the reference lower limit characteristic line by inputting the pixel value, and further calculates the adjustment upper limit value and the adjustment lower limit value obtained by adjusting the reference adjustment upper limit value and the reference adjustment lower limit value according to the degree of variation in pixel values in the partial setting region. As illustrated in FIG. 4, the emphasis processing calculation unit 25B calculates the value of the division point for dividing the adjustment upper limit value and the adjustment lower limit value by the output ratio using the input ratio that is the calculated value in the range of 0 to 1 and the calculated adjustment upper limit value and adjustment lower limit value, and outputs the calculated value of the division point as the emphasis-processed pixel value. Such emphasis processing is performed for each pixel.

Figure 7:
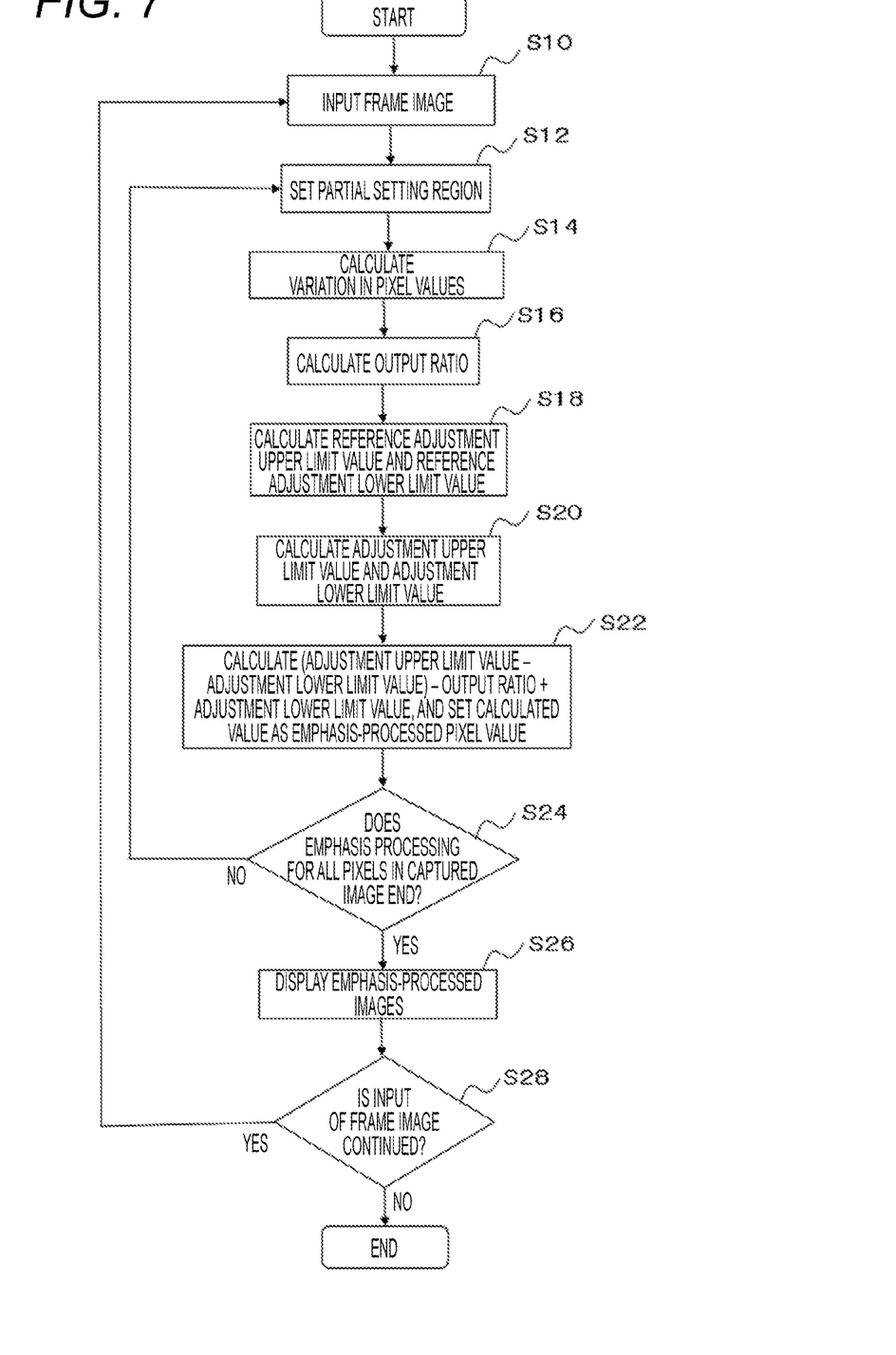
FIG. 7 is a diagram illustrating an example of a flow of the emphasis processing performed by the processor for an endoscope according to the embodiment.

FIG. 7 is a diagram illustrating an example of a flow of the emphasis processing performed by the processor according to the embodiment.

FIG. 7 illustrates an example of a flow of calculating the adjustment upper limit value and the adjustment lower limit value illustrated in FIG. 2 and performing the emphasis processing.

As illustrated in FIG. 6, first, the captured image of a current frame is input to the image processing unit 25 (step S10). Thereafter, the preprocessing unit 25A sets the partial setting region around the pixel of interest including the pixel of interest, using each pixel as the pixel of interest (step S12). For example, the partial setting region is set such that the pixel of interest becomes the center pixel. The partial setting region is, for example, a rectangular region as illustrated in FIG. 2.

Next, the preprocessing unit 25A calculates the variation in pixel values of the set partial setting region in the captured image (step S14). As the variation, for example, variance, standard deviation, absolute deviation, or difference between the maximum pixel value and the minimum pixel value of the pixel values is used as described above.

The emphasis processing calculation unit 25B calculates the output ratio by performing the nonlinear gradation conversion for the input ratio of the pixel value of the pixel of interest using the set function of the nonlinear gradation conversion as illustrated in FIG. 1 (step S16).

Moreover, the emphasis processing calculation unit 25B calculates the output pixel value of the reference upper limit characteristic line and the output pixel value of the reference lower limit characteristic line corresponding to the input pixel value using the pixel value in the partial region as the input pixel value as the reference adjustment upper limit value and the reference adjustment lower limit value as illustrated in FIG. 2, using the reference upper limit characteristic line and the reference lower limit characteristic line set in advance or set on the basis of the setting of the partial setting region (step S18). Since the reference adjustment upper limit value and the reference adjustment lower limit value can be calculated before the partial setting region is set if the reference upper limit characteristic line and the reference lower limit characteristic line have been set, step S18 can also be performed between step S10 and step S12.

The emphasis processing calculation unit 25B calculates the adjustment upper limit value and the adjustment lower limit value as illustrated in FIG. 2 by adjusting the calculated reference adjustment upper limit value and reference adjustment lower limit value according to the degree of variation in pixel values calculated in step S14 (step S20). The adjustment upper limit value is, for example, a value obtained by adding, to the reference adjustment upper limit value, a value obtained by multiplying a positive coefficient α to a value (for example, standard deviation) obtained by converting the variation in pixel values into a numeral as an adjustment value, and the adjustment lower limit value is, for example, a value obtained by adding, to the reference adjustment lower limit value, a value obtained by multiplying a negative coefficient β to a value (for example, standard deviation) obtained by converting the variation in pixel values into a numeral as an adjustment value. In this case, the adjustment upper limit value increases and the adjustment lower limit value decreases as the degree of variation increases. The coefficients α and β are set according to the set reference upper limit characteristic line and reference lower limit characteristic line.

The emphasis processing calculation unit 25B calculates the emphasis-processed pixel value using the calculated adjustment upper limit value and adjustment lower limit value and the calculated output ratio (step S22). Specifically, the emphasis processing calculation unit 25B calculates (the adjustment upper limit value−the adjustment lower limit value)*the output ratio+the adjustment lower limit value as the emphasis-processed pixel value. As illustrated in FIG. 4, the calculated value is a calculated value of the division point, which is for dividing the adjustment upper limit value and the adjustment lower limit value by the output ratio. Since (the adjustment upper limit value−the adjustment lower limit value)*the output ratio+the adjustment lower limit value can also be expressed as the output ratio*the adjustment upper limit value+(1−the output ratio)*the adjustment lower limit value, the value of the division point can also be said to be a value obtained by weighting and averaging the adjustment upper limit value and the adjustment lower limit value using the output ratio and a residual ratio obtained by subtracting the output ratio from 1 as weighting coefficients.

The image processing unit 25 determines whether all the pixels of the captured image have been emphasis-processed (step S24). In a case where a determination result is negative, the pixel of interest is moved by one pixel, the processing returns to step S12, the partial setting region is set around the pixel of interest again, and steps S14 to S24 are repeated. In this way, when the determination result becomes affirmative, the image processing unit 25 displays the emphasis-processed image on the screen of the display 5 via the result display unit 23 (step S26). Note that, in a case where the partial setting region is set by an input instruction or automatically extracted and fixed by an analysis result of the captured image, steps S14 to S22 are repeated for each partial setting region although not illustrated.

Moreover, the image processing unit 25 determines whether input of a frame image is continuously performed (step S28). When the determination is affirmative, the processing returns to step S10, and steps S10 to S28 are repeated. In this manner, the emphasis processing is repeated until the determination result becomes negative.

In this manner, the pixel value after the emphasis processing is calculated using the output ratio obtained by the nonlinear gradation conversion and the adjustment upper limit value and the adjustment lower limit value set according to the degree of variation in pixel values in the partial setting region. Therefore, although the pixel values vary, when a portion where a dark portion is collapsed by the nonlinear gradation conversion of the image is set as the partial setting region, the adjustment upper limit value increases and the adjustment lower limit value decreases due to relatively large variation in the pixel values in the dark portion. Therefore, the value of the distribution point illustrated in FIG. 4 obtained from the output ratio is likely to change in a relatively large manner with respect to the change in the input pixel value. Therefore, collapse in the dark portion is suppressed. Meanwhile, in a portion where a portion where the variation in pixel values is small is set as the partial setting region, so that the adjustment upper limit value and the adjustment lower limit value become small due to the small variation in pixel values in the partial setting region, a difference between the values also becomes small, and the pixel value sharply changes by the nonlinear conversion, the change in the value of the distribution point illustrated in FIG. 4 with respect to the change in the input pixel value is adjusted to be small, so that the emphasis of noise is suppressed.

As illustrated in FIG. 2, in the above-described embodiment, the reference adjustment upper limit value and the reference adjustment lower limit value are calculated using the reference upper limit characteristic line and the reference lower limit characteristic line set in advance, and the adjustment upper limit value and the adjustment lower limit value are calculated according to the degree of variation in pixel values in the partial setting region. However, in another embodiment, the emphasis processing calculation unit 25B may set an upper limit characteristic line and a lower limit characteristic line according to the degree of variation in pixel values in the partial setting region, as illustrated in FIG. 3. The upper limit characteristic line is a characteristic line representing an adjustment upper limit value of the output pixel value for adjusting the output pixel value output by the nonlinear gradation conversion with respect to the input pixel value, and the lower limit characteristic line is a characteristic line representing an adjustment lower limit value of the output pixel value for adjusting the output pixel value. In this case, when the pixel value is input to the emphasis processing calculation unit 25B, the adjustment upper limit value and the adjustment lower limit value are directly calculated using the upper limit characteristic line and the lower limit characteristic line. In such an embodiment, the partial setting region is set and fixed regardless of the pixel of interest, and thus it is favorable that the upper limit characteristic line and the lower limit characteristic line be lines obtained by expanding or contracting the reference upper limit characteristic line and the reference lower limit characteristic line serving as references toward the output side according to the degree of variation in pixel values in the partial setting region. Thereby, the upper limit characteristic line and the lower limit characteristic line in which the adjustment upper limit value and the adjustment lower limit value change according to the degree of variation in pixel values can be easily set. For the expansion or contraction of the reference upper limit characteristic line and the reference lower limit characteristic line to the output side according to the degree of variation, for example, the reference upper limit characteristic line and the reference lower limit characteristic line are expanded or contracted using an expansion/contraction ratio that changes according to the value indicating the degree of variation.

According to an embodiment, it is favorable that the difference between the adjustment upper limit value and the adjustment lower limit value increases as the variation in pixel values in the partial setting region increases. Thereby, the variation in pixel values increases, and thus the change in the pixel value after the emphasis processing also increases due to the change in the output ratio. Therefore, the collapse of the image of the dark portion in which the image is collapsed by the nonlinear gradation conversion is suppressed. Further, in the portion where the variation in pixel values is small, the difference between the adjustment upper limit value and the adjustment lower limit value becomes small, and thus the change in the pixel value after the emphasis processing becomes small. Therefore, emphasis of noise is suppressed.

According to an embodiment, it is favorable that the adjustment lower limit value decreases as the variation in pixel values in the partial setting region increases. Further, it is favorable that the adjustment upper limit value increases as the variation in pixel values in the partial setting region increases.

According to an embodiment, it is favorable that a change rate of the adjustment upper limit value with respect to the change in the input pixel value is not constant, but the change rate increases as the variation in pixel values in the partial setting region increases, and a change rate of the adjustment lower limit value with respect to the change in the input pixel value is not constant, but the change rate decreases as the variation in pixel values in the partial setting region increases. Thereby, the image collapse can be more effectively suppressed, and the emphasis of noise can be more effectively suppressed.

In the above-described embodiment, a conversion characteristic curve indicating the change in the output with respect to the input in the nonlinear gradation conversion illustrated in FIG. 1 is not limited to a preset curve. According to an embodiment, it is also favorable to set the conversion characteristic curve on the basis of distribution of the pixel values in the partial setting region. That is, the nonlinear gradation conversion favorably changes when the distribution of the pixel values in the partial setting region changes. As a result, the nonlinear gradation conversion is characterized according to a feature of the pixel value in the partial setting region, so that favorable emphasis processing can be implemented. For example, a histogram curve represented by a cumulative histogram obtained by normalizing a cumulative histogram of the pixel values in the partial setting region within a range of 0 to 1 can be used as the conversion characteristic curve. Furthermore, the output ratio illustrated in FIG. 1 for the pixel to be emphasis-processed can be a numerical value obtained by dividing the number of pixels having a pixel value smaller than the pixel value of the pixel to be emphasis-processed by the number of pixels in the partial setting region.

Note that the captured image captured by the endoscope 4 includes pixel values of a plurality of color components. In this case, the processing and calculation in the preprocessing unit 25A and the emphasis processing calculation unit 25B are favorably performed for each color component. At least one of the nonlinear gradation conversion, the reference upper limit characteristic line, or the reference lower limit characteristic line may be set to be different for each color component because the degree of image collapse and noise emphasis varies depending on the color component.

In the above-described embodiment, the partial setting region to be set is set for each pixel of interest, but the partial setting region may be a block region set and fixed in advance in the captured image. In this case, each of a plurality of block regions set in the captured image may be fixed in advance as the partial setting region. Since the adjustment upper limit value and the adjustment lower limit value in the emphasis processing can be changed for each partial setting region by parameters (for example, the above-described coefficients α and β) other than the variation in pixel values, the reference upper limit characteristic line, or the reference lower limit characteristic line, the emphasis processing having different characteristics can be performed for each partial setting region.

Hitherto, the processor for an endoscope and the endoscope system of the present invention are not limited to the above-described embodiments. As a matter of course, various improvements or modifications may be made within the scope not departing from the concept of the present invention.

The present invention relates to a patent application of Japanese Patent Application No. 2020-154912 filed with the Japan Patent Office on Sep. 15, 2020, the entire contents of which are incorporated herein by reference.

The invention claimed is:

1. A processor for an endoscope comprising: an image processing unit that performs gradation conversion for a captured image of a living tissue in a body cavity, wherein the image processing unit includes
an emphasis processing calculation unit configured to perform emphasis processing of an input captured image by performing nonlinear gradation conversion for a pixel value of a pixel of interest of the captured image, and
a preprocessing unit configured to set, for the input pixel value, a reference upper limit characteristic line representing a reference adjustment upper limit value of an output pixel value for adjusting the output pixel value output by the nonlinear gradation conversion and a reference lower limit characteristic line representing a reference adjustment lower limit value of the output pixel value for adjusting the output pixel value, set a partial setting region including the pixel of interest in the captured image, and calculate a degree of variation in pixel values in the partial setting region, and
the emphasis processing calculation unit
calculates an output ratio of the output pixel value to a maximum pixel value that the captured image is able to take by inputting the pixel value and performing the nonlinear gradation conversion,
calculates an adjustment upper limit value and an adjustment lower limit value by adjusting the reference adjustment upper limit value and the reference adjustment lower limit value obtained using the reference upper limit characteristic line and the reference lower limit characteristic line according to the degree of variation in pixel values by inputting the pixel value, and
calculates a value of a division point for dividing the adjustment upper limit value and the adjustment lower limit value by the output ratio, and outputs the calculated value of the division point as an emphasis-processed pixel value.

2. A processor for an endoscope comprising: an image processing unit that performs gradation conversion for a captured image of a living tissue in a body cavity, wherein
an image processing unit includes
an emphasis processing calculation unit configured to perform emphasis processing of an input captured image by performing nonlinear gradation conversion for a pixel value of a pixel of interest in a partial setting region of the captured image, and
a preprocessing unit configured to calculate a degree of variation in the pixel values in the partial setting region of the captured image, and the emphasis processing calculation unit
sets, for the input pixel value, an upper limit characteristic line representing an adjustment upper limit value of an output pixel value for adjusting the output pixel value output by the nonlinear gradation conversion and a lower limit characteristic line representing an adjustment lower limit value of the output pixel value for adjusting the output pixel value according to the degree of variation in the pixel values in the partial setting region,
calculates an output ratio of the output pixel value to a maximum pixel value that the captured image is able to take by inputting the pixel value and performing the nonlinear gradation conversion,
calculates the adjustment upper limit value and the adjustment lower limit value using the upper limit characteristic line and the lower limit characteristic line by inputting the pixel value, and
calculates a value of a division point for dividing the adjustment upper limit value and the adjustment lower limit value by the output ratio, and outputs the calculated value of the division point as an emphasis-processed pixel value.

3. The processor for an endoscope according to claim 2, wherein the upper limit characteristic line and the lower limit characteristic line are lines obtained by expanding or contracting a reference upper limit characteristic line and a reference lower limit characteristic line serving as references toward an output side according to the degree of variation.

4. The processor for an endoscope according to claim 2, wherein each of a plurality of predetermined block regions in the captured image is set as the partial setting region.

5. The processor for an endoscope according to claim 1, wherein the value of the division point is a weighted average value of the adjustment upper limit value and the adjustment lower limit value using the output ratio and a residual ratio obtained by subtracting the output ratio from 1 as weighting coefficients.

6. The processor for an endoscope according to claim 1, wherein a difference between the adjustment upper limit value and the adjustment lower limit value increases as the variation increases.

7. The processor for an endoscope according to claim 1, wherein the adjustment lower limit value decreases as the variation increases.

8. The processor for an endoscope according to claim 1, wherein the adjustment upper limit value increases as the variation increases.

9. The processor for an endoscope according to claim 1, wherein
a change rate of the adjustment upper limit value with respect to a change in the input pixel value increases as the variation increases, and
a change rate of the adjustment lower limit value with respect to a change in the input pixel value decreases as the variation increases.

10. The processor for an endoscope according to claim 1, wherein the nonlinear gradation conversion is set on a basis of a distribution of pixel values in the partial setting region.

11. The processor for an endoscope according to claim 1, wherein
the captured image includes pixel values of a plurality of color components, and
the processing and calculation in the preprocessing unit and the emphasis processing calculation unit are performed for each of the color components.

12. An endoscope system comprising:
the processor for an endoscope according to claim 1; and
an endoscope connected to the processor for an endoscope and including an image sensor that captures the living tissue.

* * * * *